United States Patent [19]

Challenger

[11] Patent Number: 5,618,970

[45] Date of Patent: Apr. 8, 1997

[54] HYDROGENATION

[75] Inventor: Stephen Challenger, Sandwich, United Kingdom

[73] Assignee: Pfizer Inc., New York, N.Y.

[21] Appl. No.: 612,940

[22] PCT Filed: Sep. 9, 1994

[86] PCT No.: PCT/EP94/03036

§ 371 Date: Mar. 7, 1996

§ 102(e) Date: Mar. 7, 1996

[87] PCT Pub. No.: WO95/08526

PCT Pub. Date: Mar. 30, 1995

[30] Foreign Application Priority Data

Sep. 22, 1993 [EP] European Pat. Off. .............. 93307517

[51] Int. Cl.$^6$ ................................................ C07C 69/74
[52] U.S. Cl. ............................................ 560/121; 560/122
[58] Field of Search ..................................... 560/121, 122

[56] References Cited

U.S. PATENT DOCUMENTS

| | | | |
|---|---|---|---|
| 4,194,051 | 3/1980 | Bachmann . | |
| 4,962,230 | 10/1990 | Takaya | 562/433 |
| 5,192,800 | 3/1993 | Barnish . | |
| 5,334,758 | 8/1994 | Saburi | 562/590 |

FOREIGN PATENT DOCUMENTS 342850  11/1989  European Pat. Off. .

OTHER PUBLICATIONS

Chemistry in Britain, Apr. 1993, p. 319.

*Primary Examiner*—Michael L. Shippen
*Attorney, Agent, or Firm*—Peter C. Richardson; Gregg C. Benson; Robert T. Ronau

[57] ABSTRACT

Compounds of formula

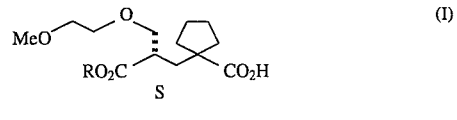

or

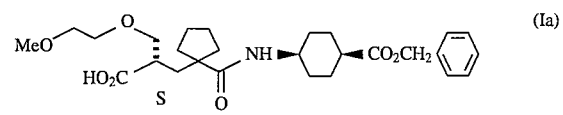

where R is 5-indanyl or a carboxylic acid protecting group, or an amine salt thereof, are prepared by hydrogenating an (E)-allylic ether of formula

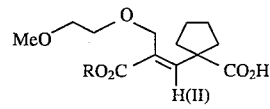

or

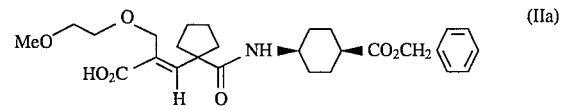

in the presence of a stereoselective rhodium or ruthenium biphosphine catalyst and a protic solvent.

22 Claims, No Drawings

HYDROGENATION

This is the national stage under 35 U.S.C. §371(c) and 37 C.F.R. §1.491 of International Application No. PCT/EP94/03036, having the international filing date of Sep. 9, 1994, which was originally filed Sep. 22, 1993 as Great Britain Patent Application No. 93307517.8.

This invention relates to preparation of compounds which are useful as intermediates in preparation of spiro-substituted glutaramide derivatives, notably the compound having the approved non-proprietary name candoxatril and the systematic name (S)-cis-4-(1-[2-(5-indanyloxycarbonyl)-3-(2-methoxyethoxy)propyl]-1-cyclopentane carboxamido)-1-cyclohexanecarboxylic acid. This compound is among those mentioned in U.S. Pat. No. 5,192,800 as inhibitors of the neutral endopeptidase E.C.3,4.24.11 enzyme useful in therapy as diuretic agents for the treatment of hypertension, heart failure, renal insufficiency and other disorders.

Candoxatril may be prepared by coupling the (S)-enantiomer of a compound of formula (I):

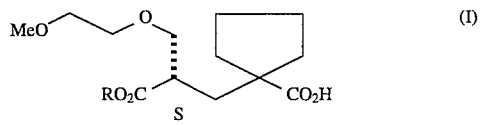

wherein R is 5-indanyl or a carboxylic acid protecting group, with cis-4-amino-cyclohexane-carboxylic acid benzyl ester, followed by hydrogenation to remove the benzyl group. When R is a 5-indanyl group this procedure produces candoxatril; when R is another group it may be removed and replaced by a 5-indanyl group by conventional methods.

The compound of formula (I) is the (S)-enantiomer of the chiral glutaric acid derivative shown and the substantially optically pure enantiomer is required for manufacture of candoxatril which is itself an enantiomer of a chiral compound. As described in U.S. Pat. No. 5,192,800 (Example 431 et seq) the (S)-enantiomers of formula (I) may be prepared by resolution of its racemate with (1S,2S)-(+)-pseudoephedrine. This resolution process is inefficient.

The present invention is intended to provide a method of providing the (S) enantiomers of compounds of formula (I) by asymmetric hydrogenation of a corresponding (E)-allylic ether.

According to the invention, there is provided a method of preparing the (S) enantiomer of a compound of formula (I):

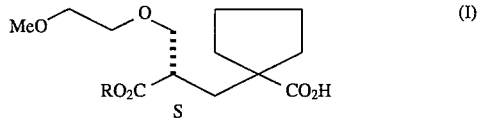

or an amine salt thereof, wherein R is 5-indanyl or a carboxylic acid protecting group, which comprises hydrogenating an (E)-allylic ether of formula (II):

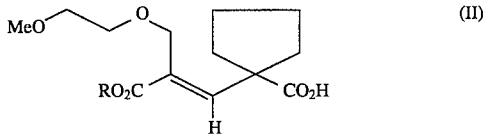

or an amine salt thereof wherein R is as defined for formula (I), in the presence of a stereoselective chiral rhodium or ruthenium biphosphine catalyst capable of catalysing said hydrogenation and a protic solvent.

R may be a straight or branched $C_1$–$C_4$ alkyl group such as a t-butyl group.

Several chiral biphosphine catalysts containing rhodium or ruthenium are known and are either commercially available or may be made by methods known in the art. They contain rhodium or ruthenium species complexed with chiral biphosphine ligands such as 2,2'bis(diphenylphosphino)-1, 1'-binaphthyl (generally known as BINAP), t-butyl-4-(diphenyl phosphino)-2-(diphenylphosphino)-2-(diphenylphosphinomethyl)-1-pyrrolidinecarboxylate (known as BPPM) and 1,2-bis(diphenylphosphino)propane (known as PROPHOS). Being chiral, these ligands exist in (R)- and (S)-forms and their complexes with metals such as rhodium and ruthenium are themselves chiral. It has been found that some, but not all, of these catalysts are capable of giving stereoselective reduction of the allylic ethers of formula (II).

These catalysts may be obtained commercially or prepared by known methods. Alternatively, they may be prepared in situ in known manner.

The hydrogenation may be carried out in known manner by exposing a solution of the allylic ether to hydrogen gas, typically at a pressure of about 60 psi, in the presence of the catalyst. A reaction temperature of up to 50° C. is generally suitable, at higher temperatures decarboxylation of the acid of formula (II) may occur. The solvent used should be a protic solvent: methanol and aqueous methanol have been found suitable. Substantially no reduction took place in aprotic solvents such as toluene and dimethylformamide.

R may be a $C_1$–$C_4$ alkyl group, such as t-butyl.

One class of catalysts which may be used are the biphosphine complexes of BINAP with rhodium and ruthenium, such as the complexes of BINAP and p-cymene with ruthenium chloride and of BINAP with 1,5-cyclo octadiene and rhodium chloride. It has been found that the (R)-(+) enantiomer of the biphosphine ligand is required to produce the desired (S)-enantiomer of the formula (I) compound when the catalyst contains ruthenium; the (S)-(–) enantiomer is required with rhodium.

Of other known types of catalyst, a chloride complex of rhodium with (S)-(–) BPPM also yields the (S)-enantiomer of the formula (II) compound.

A chloride complex of rhodium with R-(+)-PROPHOS gave both S- and R-enantiomers of the formula (I) compound with a greater proportion of the S-enantiomer. However a complex of rhodium with (S,S)-(+)-2,3-O-isopropylidene-2,3-dihydroxy-1,4-bis(diphenylphosphino)-butane gave a greater proportion of the R-enantiomer.

It has also been found that the identity of the acid or amine has an affect on the hydrogenation reaction. With the(R)-BINAP ruthenium catalyst, when $R^1$ is t-butyl, the compound of formula (II) obtained is predominantly the (S)-enantiomer when the starting material is the acid of formula (II) or its amine salt; when the (S)-BINAP rhodium catalyst is used the salt gives a high yield of(S)-enantiomer of formula (II) but the free acid of formula (II) does not.

Suitable amine salts are the cyclohexamine and the (1S, 2S)-pseudoephedrine salt.

Another aspect of the invention provides a method of preparing the (S) enantiomer of a compound of formula (Ia):

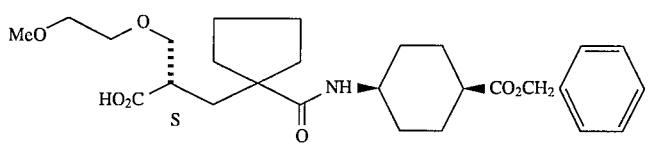

(Ia)

which comprises hydrogenating an (E)-allylic ether of formula (IIa):

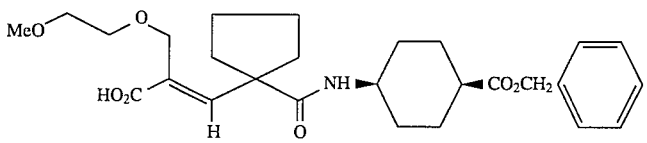

(IIa)

in the presence of a stereoselective chiral rhodium or ruthenium biphosphine catalyst capable of catalysing said hydrogenation, and a protic solvent.

In the latter aspect of the invention the preferred catalyst is the (R-)BINAP/p-cymene ruthenium catalyst mentioned above. The preferred hydrogenation conditions are the same as for the compounds of formula (I).

The starting materials (II) for the above syntheses may be prepared according to the following reaction scheme:

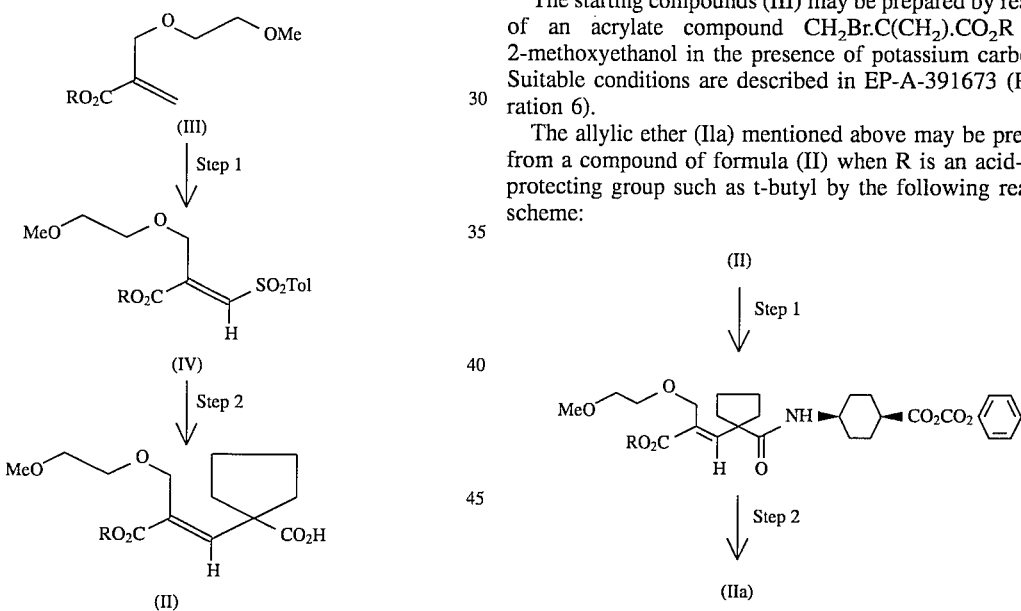

In step 1 of this scheme a compound of formula (III) where R is as defined above for formula (II) is allowed to react with p-toluenesulphonyl iodide and then treated with a base such as triethylamine to remove hydrogen iodide, to yield the vinyl sulphone (IV). The p-toluenesulphonyl iodide may be formed in situ from iodine and benzenesulphinic acid or a salt thereof, such as the sodium salt and the reaction may be conducted in a solvent such as ethyl acetate. This reaction is stereospecific and the stereochemistry of the compound (IV) is trans(E), confirmed by X-ray analysis.

Compound (IV) may be separated by conventional methods and, in step 2, converted to compound (II) by treatment with a zinc-modified dianion of cyclopentanecarboxylic acid followed by removal of p-toluene sulphinate salt. This reaction may be conducted by treating cyclopentanecarboxylic acid with lithium diisopropylamide in an inert solvent such as tetrahydrofuran, adding a solution of zinc chloride in diethyl ether followed by compound (IV) in a solvent such as tetrahydrofuran, and subsequently adding aqueous acid followed by pH adjustment and extraction with an organic solvent to yield compound (II). This reaction is highly stereoselective and proceeds with retention of configuration, yielding the (E)-enantiomer of the allylic ether (II).

In this synthesis the p-toluene sulphonyl iodide may be replaced by its aryl analogues such as benzene, 4-chlorobenzene, 4-bromobenzene and 4-nitrobenzene sulphonyl halides.

The starting compounds (III) may be prepared by reaction of an acrylate compound $CH_2Br.C(CH_2).CO_2R$ with 2-methoxyethanol in the presence of potassium carbonate. Suitable conditions are described in EP-A-391673 (Preparation 6).

The allylic ether (IIa) mentioned above may be prepared from a compound of formula (II) when R is an acid-labile protecting group such as t-butyl by the following reaction scheme:

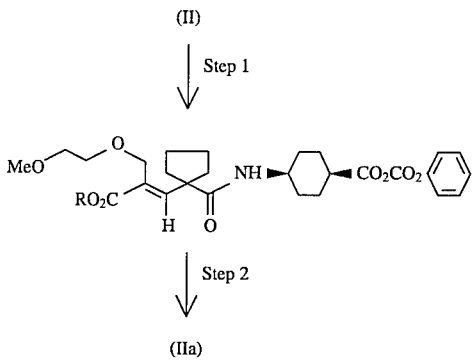

In step 1 of this scheme the formula (II) compound may be treated with thionyl chloride and then with benzyl-cis-4-amino-1-cyclohexane carboxylate-p-toluenesulphonate in the presence of a base such as triethylamine in a solvent such as ethyl acetate. The product may be separated and then treated with a strong acid such as trifluoroacetic acid in step 2 to remove the R group and yield compound (IIa).

Preparation of compounds according to the invention and certain intermediates is illustrated by the following Examples and Preparations.

EXAMPLE 1

(S)-1-[2-(tert-Butoxycarbonyl)-3-(2-methoxyethoxy)-propyl]-1-cyclopentanecarboxylic acid cyclohexylamine salt (E)-1-[2-(tert-Butoxycarbonyl)-3-(2-methoxyethoxy)prop-1-enyl]-1-cyclopentanecarboxylic acid cyclohexylamine salt (50 g, 0.117 mole) and [(R)-(+)-2,2'-bis(diphenylphosphino)-1,1'-binaphthyl]chloro(p-cymene)ruthenium chloride (108 mg, 0.11 mmole) were charged to a 500 mL glass Dreschel bottle containing a magnetic stirrer bar and the top sealed with a rubber septum. The system was purged with nitrogen, methanol (300 mL) and deoxygenated demineralised water (100 mL) were added and the mixture sparged with nitrogen for 2 hours. The mixture was hydrogenated inside a steel bomb at 60 p.s.i. and at 45°–50° C. for 19 hours. The solvents were removed under reduced pressure and the crude product dissolved in ethyl acetate (345 mL) at reflux, diluted with hexane (345 mL) and allowed to cool to room temperature. The precipitated salt was granulated for 16 hours at room temperature and collected to give the title compound (33.33 g, 68%) (ratio S:R 99:1) m.pt= 120°–122° C., $R_f$=0.3 (ethyl acetate/hexane, 1:1+1% acetic acid).

$^{13}$C NMR (75.4 Hz, CDCl$_3$): δ=24.69, 25.10, 25.15, 27,99, 32.75, 34.79, 37.26, 38.02, 45.05, 50.14, 54.61, 58.86, 70.07, 71.82, 73.59, 80.06, 174.79 and 183.08 ppm.

EXAMPLE 2

(S)-1-[2-(tert-Butoxycarbonyl)-3-(2-methoxyethoxy)propyl]-1-cyclopentanecarboxylic acid cyclohexylamine salt (E)-1-[2-(tert-Butoxycarbonyl)-3-(2-methoxyethoxy)prop-1-enyl]-1-cyclopentanecarboxylic acid cyclohexylamine salt (5.0 g, 11.7 mmole) and [(R)-(+)-2,2'-bis (diphenylphosphino)-1,1'-binaphthyl]chloro(p-cymene)ruthenium chloride (10.9 mg, 0.011 mmol) were charged to a 100 mL glass bottle and the top sealed with a rubber septum. The system was purged with dry hydrogen, methanol (50 mL) was added and the mixture purged with nitrogen for 3 hours. The mixture was hydrogenated inside a steel bomb at 60 p.s.i. and at 45°–50° C. for 50 hours. The methanol was removed under reduced pressure and the crude product dissolved in ethyl acetate (35 mL) at. reflux, diluted with hexane (35 mL) and allowed to cool to room temperature. The precipitated salt was granulated for 16 hours at room temperature and collected to give the title compound identical to that of Example 1 (3.17 g, 63%) (ratio S:R 99:1) $R_f$=0.33 (ethyl acetate/hexane, 1:1+1% acetic acid).

EXAMPLE 3

(S)-1-[2-(tert-Butoxycarbonyl)-3-(2-methoxyethoxy)propyl]-1-cyclopentanecarboxylic acid (E)-1-[2-(tert-Butoxycarbonyl)-3-(2-methoxyethoxy)prop-1-enyl]-1-cyclopentanecarboxylic acid (0.2 g, mmole) and [(R)-(+)-2,2'-bis(diphenylphosphino)-1,1'-binaphthyl]chloro(p-cymene)ruthenium chloride (11.3 ml, mmol) were charged to a glass vial and the top sealed with a rubber septum. The system was purged with nitrogen, methanol (5 mL) was added and the mixture sparged with nitrogen for 3 hours. The mixture was hydrogenated inside a steel bomb at 414 kPa (60 p.s.i.) and at 45°–50° C. for 26 hours. The methanol was removed under reduced pressure to give the title compound (67% by NMR) (ratio S:R 98:2), $R_f$=0.29 (ethyl acetate/hexane, 1:1+1% acetic acid).

$^1$H NMR (300 MHz, CDCl$_3$): δ=1.43(s,9H), 1.45–1.57(m, 2H), 1.65–1.68(m,4H), 1.80(dd,1H), 1.99(dd,1H), 2.09–2.16(m,2H), 2.57–2.66(m,1H), 3.36(s,3H), 3.40–3.61 ppm (m,6H).

$^{13}$C NMR (75.4 MHz, CDCl$_3$): δ=24.54, 24.90, 27.93, 35.10, 36.61, 37.38, 44.56, 53.46, 58.91, 70.16, 71.81, 73.30, 80.56, 173.98, 183.41 ppm.

EXAMPLE 4

(R)-1-[2-(tert-Butoxycarbonyl)-3-(2-methoxyethoxy)propyl]-1-cyclopentanecarboxylic acid (E)-1-[2-(tert-Butoxycarbonyl)-3-(2-methoxyethoxy)propyl-1-enyl]-1-cyclopentanecarboxylic acid cyclohexylamine salt (0.1 g, 0.22 mmoles) and RuHCl[(S)-(−)-2,2'-bis(diphenylphosphino)-1,1'-binaphthyl]$_2$ (8.5 mg, 0.0061 mmole) were charged to a glass vial containing a magnetic stirrer bar and the top sealed with a rubber septum. The system was purged with argon, methanol (2.5 mL) was added and the mixture hydrogenated inside a steel bomb at 345 kPa (50 p.s.i.) and room temperature for 48 hours. The reaction mixture was purged with nitrogen, filtered and the methanol removed under reduced pressure. The crude product was partitioned between hexane (10 mL) and 1.0M aqueous hydrochloric acid solution (10 mL) and the layers separated. The aqueous layer was further extracted with hexane (2×10 mL) and the combined hexane extracted dried (MgSO$_4$), filtered and concentrated to give the title compound as an oil (37 mg, 51%) (ratio S:R 9:91).

EXAMPLE 5

(S)-1-[2-(tert-Butoxycarbonyl)-3-(2-methoxyethoxy)propyl]-1-cyclopentanecarboxylic acid cyclohexylamine salt Chloro(1,5-cyclooctadiene)rhodium(I)dimer (15.2 mg, 0.03 mmole) and (S)-(−)-2,2'-bis(diphenylphosphino)-1,1'-binaphthyl (42.2 mg, 0.06 mmole) were charged to a 50 mL three necked flask equiped with gas inlet and outlet lines and the third neck sealed with a rubber septum. The system was flushed with nitrogen, methanol (10 mL) was added and the mixture purged with nitrogen for 30 minutes. The reaction was hydrogenated at atmospheric hydrogen pressure and room temperature for 1 hour. At this point a solution of (E)-1-[2-(tert-butoxycarbonyl)-3-(2-methoxyethoxy)prop-1-enyl]-1-cyclopentanecarboxylic acid cyclohexylamine salt (0.5 g, 1.17 mmol) in methanol (10 mL) was added and the mixture hydrogenated at atmospheric pressure and room temperature for 5 days. The reaction mixture was purged with nitrogen and concentrated under reduced pressure to give a brown solid (Ratio S:R 89:11). The crude product was recrystallised from ethyl acetate (3.5 ml) and hexane (3.5 ml) to give the title compound (0.37 g, 74%). (Ratio S:R 92:8), $R_f$=0.29 (ethyl acetate/hexane, 1:1+1% acetic acid).

EXAMPLE 6

(S)-1-[2-(tert-Butoxycarbonyl)-3-(2-methoxyethoxy)propyl]-1-cyclopentanecarboxylic acid (1S,2S)-(+)-pseudoephedrine salt Chloro(1,5-cyclooctadiene)rhodium(I)dimer (3.0 mg, 0.006 mmole) and (S)-(−)-2,2'-bis(diphenylphosphino)-1,1'-binaphthyl (3.8 mg, 0.006 mmole) were charged to a glass vial and the top sealed with a rubber septum. The system was purged with argon, methanol (1.0 mL) was added followed by a solution of (E)-1-[2-(tert-butoxycarbonyl)-3-(2-methoxyethoxy)prop-1-enyl]-1-cyclopentanecarboxylic acid (1S,2S)-(+)-pseudoephedrine salt (0.1 g, 0.2 mmoles) in methanol(1.5 mL). The mixture was hydrogenated inside a steel bomb at 345 kPa (50 p.s.i.) and room temperature for 48 hours. The reaction mixture was purged with nitrogen and the methanol removed by evaporation under reduced pressure to give the title compound as an oil (0.1 g, quantitative crude yield) (ratio S:R 90:10).

$^1$H NMR (300 MHz, CDCl$_3$): δ=1.02(d,3H), 1.40–1.49(m,2H), 1.43(s,9H), 1.59–1.67(m,4H), 1.77(dd, 1H), 1.88(dd,1H), 2.06–2.18(m,2H), 2.57(s,3H), 2.61–2.71 (m, 1H), 2.86–2.97(m, 1H), 3.29(s,3H), 3.43–3.59(m,6H), 4.47(d, 1 H), 6.17(brs,3H), 7.27–7.38(m,5H) ppm.

$^{13}$C NMR (75.4 Hz, CDCl$_3$): δ=13.38, 24.62, 27.90, 30.71, 34.95, 37.44, 38.17, 45.18, 54.82, 58.85, 60.74, 70.05, 71.80, 73.66, 75.63, 80.04, 127.13, 127.99, 128.45, 141.30, 174.80, 184.00 ppm.

Analysis %: Found: C,65.53; H,9.17; N,3.22. C$_{27}$H$_{45}$NO$_7$ C,65.43; H,9.15; N,2.83.

EXAMPLE 7

(S )-1-[2-(tert-Butoxycarbonyl)-3-(2-methoxyethoxy)propyl]-1-cyclopentanecarboxylic acid (E)-1-[2-(tert-Butoxycarbonyl)-3-(2-methoxyethoxy)prop-1-enyl]-1-cyclopentanecarboxylic acid cyclohexylamine salt (100 mg, 0.22 mmole), chloro(1,5-cyclooctadiene)rhodium(I)dimer (3.0 mg, 0.0006 mmole) and (2S,4S)-tert-butyl-4-(diphenylphosphino)-2-(diphenylphosphino)-2-(diphenylphosphinomethyl)-1-pyrrolidinecarboxylate (7.6 mg, 0.013 mmole) were charged to a glass vial and the top sealed with a rubber septum. The system was purged with argon, methanol (2.5 mL) was added and the mixture purged with argon for 30 minutes. The reaction was hydrogenated at 104 kPa (15 p.s.i.) and room temperature for 20.5 hours. The reaction mixture was purged with nitrogen, Dowex 50W-X2 ion exchange resin (200 mesh, 100 mg) added and the mixture stirred for 15 minutes. The ion exchange resin was removed by filtration and the methanol removed by evaporation under reduced pressure to give the title compound as an oil (73 mg, quantitative) (ratio S:R 61:39), R$_f$=0.3 (ethyl acetate/hexane, 1:1+1% acetic acid).

EXAMPLE 8

(E)-1-[2-(tert-Butoxycarbonyl)-3-(2-methoxyethoxy)propyl]-1-cyclopentanecarboxylic acid (E)-1-[2-(tert-Butoxycarbonyl)-3-(2-methoxyethoxy)prop-1-enyl]-1-cyclopentanecarboxylic acid cyclohexylamine salt (50 mg, 0.11 mmoles) was charged to a glass vial and the top sealed with a rubber septum. Ethanol (0.33 mL) was added followed by a solution of chloro(1,5-cyclooctadiene)rhodium(I)dimer (2.0 mg, 0.004 mmoles) and (+)-2,3-O-isopropylidene-2,3-dihydroxy-1,4-bis(diphenylphosphino)butane (3.9 mg, 0.008 mmoles) in toluene (0.17 mL) and the mixture sparged with nitrogen. The mixture was hydrogenated in a steel bomb at 345 kPa (50 p.s.i.) and room temperature for 24 hours, diluted with ethyl acetate (50 mL) and 2.0N aqueous hydrochloric acid solution (50 mL) and the layers separated. The ethyl acetate layer was passed through a plug of silica gel and concentrated under reduced pressure to give the title compound as a yellow-brown oil (37 mg) (ratio R:S 62:38), R$_f$=0.3 (ethyl acetate/hexane, 1:1+1% acetic acid).

EXAMPLE 9

(S)-1-[2-(tert-Butoxycarbonyl)-3-(2-methoxyethoxy)propyl]-1-cyclopentanecarboxylic acid (E)-1-[2-(tert-Butoxycarbonyl)-3-(2-methoxyethoxy)prop-1-enyl]-1-cyclopentanecarboxylic acid cyclohexylamine salt (50 mg, 0.11 mmole), chloro(1,5-cyclooctadiene)rhodium(I)dimer (2.0 mg, 0.004 mmole) and (R)-(+)-1,2-bis(diphenylphosphino)propane (3.2 mg, 0.008 mmole) were charged to a glass vial and the top sealed with a rubber septum. The system was flushed with argon, methanol (0.5 mL) was added and the mixture hydrogenated in a steel bomb at 345 kPa (50 p.s.i.) and room temperature for 4 hours. The crude product was purified by chromatography on silica by eluting with diethyl ether/1% acetic acid to give, after combination and evaporation of appropriate fractions, the title compound as an oil, (22 mg, 61%) (ratio S:R 54.46), R$_f$=0.3 (ethyl acetate/hexane, 1:1+1% acetic acid).

EXAMPLE 10

(S)-Benzyl cis-4-{1-[2-carboxy-3-(2-methoxyethoxy)propyl]-1-cyclopentanecarboxamido}-1-cyclohexanecarboxylate (E)-Benzyl cis-4-{1-[2-carboxy-3-(2-methoxyethoxy)prop-1-enyl]-1-cyclopentanecarboxamido}-1-cyclohexanecarboxylate (100 mg, 0.2 mmole) and [(R)-(+)-2,2'-bis(diphenylphosphino)-1,1'-binaphthyl]chloro(p-cymene)ruthenium chloride (3.8 mg, 0.004 mmole) were charged to a vessel containing a magnetic stirrer bar and the top sealed with a rubber septum. The system was purged with nitrogen, methanol (5 mL) was added and the mixture sparged with nitrogen for 2 hours. The mixture was hydrogenated inside a steel bomb at 414 kPa (60 p.s.i.) and at 45°–50° C. for 16 hours. The methanol was removed under reduced pressure to give the title compound (113 mg, quantitative) (ratio S:R 85:15).

PREPARATIONS (E)-tert-Butyl 2-(2-methoxyethoxymethyl)-3-(benzenesulphonyl)acrylate To a suspension of benzenesulphinic acid sodium salt (7.59 g, 46.2 mmol) and tert-butyl 2-(2-methoxyethoxymethyl)acrylate (10.0 g, 46.2 mmol) in ethyl acetate (50 mL) under a nitrogen atmosphere at room temperature was added, in one portion, iodine (11.3 g, 46.2 mmol) and the mixture stirred for 3 days. An additional 50 mL of ethyl acetate was added after 2 days. The reaction mixture was cooled to 0° C. and triethylamine (9.67 mL, 69.3 mmol) added dropwise. The reaction was stirred at 0° C. for 2 hours and at room temperature for 16 hours and diluted with distilled water (100 mL) and ethyl acetate (50 mL). The layers were separated and the aqueous layer further extracted with ethyl acetate (25 mL). The combined ethyl acetate extracts were washed with a 1.0M aqueous hydrochloric acid solution and 5% aqueous sodium thiosulphate solution (2×100 mL), filtered to remove solids and the filter pad washed with ethyl acetate. The combined filtrate and washings were washed with distilled water (50 mL), and concentrated under reduced pressure to give a brown oil, (14.85 g). The crude product was purified by chromatography on silica by eluting with hexane/ethyl acetate (2:1) to give, after combination and evaporation of appropriate fractions, the title compound as an oil, (5.09 g, 30.8%) which crystallised on standing, m.pt.=46°–48° C., $R_f$=0.25 (silica, hexane/ethyl acetate, 2:1), (MH$^+$ 357.05, 1.7%).

$^1$H NMR (300 MHz, CDCl$_3$): δ=1.47(s,9H), 3.35(s,3H), 3.35–3.53(m,2H), 3.63–3.66(m,2H), 4.75(s,2H), 7.03(s,1H), 7.54–7.59(m,2H), 7.63–7.68(m, 1H), 7.96(d,2H).

$^{13}$C NMR (75.4 MHz): δ=27.84, 58.90, 62.94, 70.39, 71.66, 83.38, 128.02, 129.45, 134.05, 137.56, 140.21, 142.91, 163.89 ppm.

Analysis %: Found: C,57.11; H,7.08. C$_{17}$H$_{24}$O$_6$S requires: C,57.29; H,6.79.

(E)-tert-Butyl 2-(2-methoxyethoxymethyl)-3-(p-toluenesulphonyl)acrylate

To a solution of p-toluenesulphonyl iodide (19.39 g, 68.7 mmol) in dichloromethane (50 mL) at room temperature under a nitrogen atmosphere was added tert-butyl 2-(2-methoxyethoxymethyl)acrylate (9.91 g, 45.8 mmol). The mixture was stirred at room temperature for 16 hours, cooled to 0° C. and triethylamine (12.7 mL, 91.6 mmol) added dropwise. The reaction was stirred at 0° C. for 0.5 hours and at room temperature for 4 hours, diluted with distilled water (100 mL) and the layers separated. The aqueous layer was further extracted with dichloromethane (25 mL) and the combined organic extracts were washed with 1.0M aqueous hydrochloric acid solution (100 mL), 5% aqueous sodium thiosulphate solution (25 mL) and distilled water (50 mL). The dichloromethane phase was concentrated under reduced pressure to give a brown oil (17.48 g, quantitative). The crude product was purified by chromatography on silica by gradient elution with hexane/ethyl acetate mixtues to give, after combination and evaporation of appropriate fractions, the title compound as a pale yellow oil (16.2 g, 95%) which crystallised on standing, m.pt.=40°–41° C., $R_f$=0.3 (silica; hexane/ethyl acetate, 2:1).

$^1$H NMR (300 MHz, CDCl$_3$): δ=1.47(s,9H), 2.45(s,3H), 3.36(s,3H), 3.51–3.54(m,2H), 3.63–3.67(m,2H), 4.75(brs, 2H), 7.02(brs,1H), 7.35(d,J=9 Hz,2H), 7.84 ppm (d,J=9 Hz,2H).

$^{13}$C NMR (75.4 MHz, CDCl$_3$): δ=21.65, 27.84, 58.87, 62.90, 70.34, 71.66, 83.24, 128.04, 130.08, 137.29, 137.90, 142.37, 145.23, 163.96 ppm.

Analysis %: Found: C,58.51; H,7.20. C$_{18}$H$_{26}$O$_6$S C,58.36; H,5.93.

(E)-tert-Butyl 2-(2-methoxyethoxymethyl)-3-(4-chlorobenzenesulphonyl)acrylate To a solution of 4-chlorobenzenesulphonyl iodide (4.95 g, 16.4 mmol) in dichloromethane (12 mL) at room temperature was added tert-butyl 2-(2-methoxyethoxymethyl)acrylate (2.36 g, 10.9 mmol). The mixture was stirred at room temperature for 23 hours, cooled to 0° C. and triethylamine (2.9 mL, 21.8 mmol) added dropwise. The reaction was stirred at 0° C. for 1.25 hours, diluted with distilled water (25 mL) and dichloromethane (12 mL) and the layers separated. The aqueous layer was further extracted with dichloromethane (10 mL) and the combined organic extracts were washed with 1.0M aqueous hydrochloric acid solution (25 mL), 5% aqueous sodium thiosulphate solution (25 mL) and distilled water (10 mL). The dichloromethane phase was concentrated under reduced pressure to give a brown oil (4.46 g). The crude product was purifed by chromatography on silica by eluting with hexane/ethyl acetate (3:1) to give, after combination and evaporation of appropriate fractions, the title compound as a oil, (3.50 g, 82%), $R_f$=0.38 (silica, hexane/ethyl acetate, 2:1).

$^1$H NMR (300 MHz, CDCl$_3$): δ=1.48(s,9H), 3.37(s,3H), 3.51–3.54(m,2H), 3.64–3.68(m,2H), 4.74(s,2H), 7.02(s,1H), 7.53(d,J=9 Hz,2H), 7.92(d,J=9 Hz, 2H).

$^{13}$C NMR (75.4 MHz, CDCl$_3$): δ=27.71, 58.84, 62.56, 70.34, 71.51, 83.50, 129.51, 129.73, 137.37, 138.32, 140.88, 142.84, 163.58 ppm.

Analysis %: Found: C,52.26; H,5.91. C$_{17}$H$_{23}$ClO$_6$S C,52.24; H,5.93.

(E)-tert-Butyl 2-(2-methoxyethoxymethyl)-3-(4-bromobenzenesulphonyl)acrylate To a solution of 4-bromobenzenesulphonyl iodide (1.06 g, 3.15 mmol) in dichloromethane (4.5 mL) at room temperature was added tert-butyl 2-(2-methoxyethoxymethyl)acrylate (0.45 g, 2.1 mmol). The mixture was stirred at room temperature for 2.5 hours, cooled to 0° C. and triethylamine (0.58 mL, 4.2 mmol) added dropwise. The reaction was stirred at 0° C. for 0.5 hours and at room temperature for 1.0 hour, diluted with distilled water (20 mL) and dichloromethane (15 mL) and the layers separated. The aqueous layer was further extracted with dichloromethane (2×5 mL) and the combined organic extracts were washed with 1.0M aqueous hydrochloric acid solution (20 mL), 5% aqueous sodium thiosulphate solution (20 mL) and distilled water (20 mL). The dichloromethane phase was dried (MgSO$_4$), filtered and concentrated under reduced pressure to give a brown oil (0.88 g). The crude product was purified by chromatography on silica by gradient elution with hexane/ethyl acetate mixtures to give, after combination and evaporation of appropriate fractions, the title compound as a yellow oil (0.75 g, 83%), $R_f$=0.39 (silica; hexane/ethyl acetate, 2:1).

$^1$H NMR (300 MHz, CDCl$_3$): δ=1.47(s,9H), 3.37(s,3H), 3.50–3.55(m,2H), 3.63–3.67(m,2H), 4.71(s,2H), 7.01(s,1H), 7.70(d,J=8 Hz,2H) and 7.85(d,J=8 Hz,2H) ppm.

Analysis %: Found: C,46.71; H,5.26. C$_{17}$H$_{23}$BrO$_6$S C,46.90; H,5.33.

(E)-tert-Butyl 2-(2-methoxyethoxymethyl)-3-(4-nitrobenzenesulphonyl)acrylate To a solution of 4-nitrobenzenesulphonyl iodide (1.49 g, 4.65 mmol) in dichloromethane (6 mL) at room temperature was added tert-butyl 2-(2-methoxyethoxymethyl)acrylate (0.68 g, 3.1 mmol). The mixture was stirred at room temperature for 3.5 hours and triethylamine (0.88 mL, 6.2 mmol) added dropwise. The reaction was stirred for 16 hours, diluted with distilled water (25 mL) and dichloromethane (10 mL) and the layers separated. The aqueous layer was further extracted with dichloromethane (5 mL) and the combined organic extracts were washed with 1.0N aqueous hydrochloric acid solution (20 mL), 5% aqueous sodium thiosulphate solution (20 mL) and distilled water (20 mL). The dichloromethane phase was dried (MgSO$_4$), filtered and concentrated under reduced pressure to give a brown oil (1.20 g). The crude product was purified by chromatography on silica by gradient elution with hexane/ethyl acetate mixtures to give, after combination and evaporation of appropriate fractions, the title compound as a yellow oil (0.78 g, 61.9%), $R_f$=0.33 (silica; hexane/ethyl acetate, 2:1), (MH$^+$ 402.88, 1.07%).

$^1$H NMR (300 MHz, CDCl$_3$): δ=1.48(s,9H), 3.37(s,3H), 3.51–3.54(m,2H), 3.66–3.69(m,2H), 4.74(s,2H), 7.05(s,1H), 8.21(d,J=9 Hz,2H), 8.39(d,J=9 Hz,2H) ppm.

$^{13}$C NMR (75.4 Hz, CDCl$_3$): δ=27.83, 58.93, 62.71, 70.76, 71.67, 83.88, 124.57, 129.65, 136.58, 144.65, 145.67, 150.96 and 163.32 ppm.

Analysis %: Found: C,50.75; H,5.80; N,3.46. C$_{17}$H$_{23}$NO$_8$S C,50.86; H,5.77; N,3.49.

(E)-1-[2-(tert-Butoxycarbonyl)-3-(2-methoxyethoxy)prop-1-enyl]-1-cyclopentanecarboxylic acid cyclohexylamine salt To a solution of diisopropylamine (216 mL, 1.54 mol) in anhydrous THF (4.0 L) at −10° C. under a nitrogen atmosphere was added dropwise over a period of 35 minutes a 1.6M solution of n-butyllithium (9.66 mL, 1.54 mol) in hexane. The reaction was stirred at −10° C. for 15 minutes and allowed to warm to 0° C. over a period of 45 minutes. At this point cyclopentanecarboxylic acid (84 mL, 0.77 mole) was added over 30 minutes maintaining the temperature below 0° C. by external cooling. The reaction mixture was allowed to warm to room temperature oer 1.25 hours, cooled to 0° C. and a 1.0M solution of zinc chloride in diethyl ether (422 mL, 0.42 mol) added over a period of 10 minutes. The reaction was stirred at 0° C. for 25 minutes, cooled to −20° C. and a solution of (E)-tert-butyl 2-(2-methoxyethoxymethyl)-3-(p-toluenesulphonyl)acrylate (260 g, 0.70 mol) in anhydrous THF (530 mL) added. The reaction was stirred at −20° to 0° C. for 16 hours, diluted with concentrated hydrochloric acid (214 mL) and the adjusted to 5 with 5.0N aqueous sodium hydroxide solution (2 mL). The mixture was filtered to remove insolubles, extracted with ethyl acetate (1.3 L) and the layers separated. The ethyl acetate layer was washed with 1.0M aqueous hydrochloric acid solution (2.61 L), distilled water (2×2.6 L) and concentrated under reduced pressure to give an oil (259.8 g). The crude product was dissolved in hexane (2.25 L) at reflux, the heating was removed and cyclohexylamine (78.5 mL, 0.68 mol) was added. The mixture was diluted with hexane (1.13 L) and the precipitated salt cooled to 0° C. granulated for 1 hour and collected to give the title compound (209.9 g, 70%) m.pt.=108°–108° C., R$_f$=0.28 (ethyl acetate/hexane, 1:1+1% acetic acid).

$^1$H NMR (300 MHz, CDCl$_3$): δ=3.36(s, 3H), 3.50–3.53(m,2H), 3.58–3.61(m,2H), 4.24(s,2H), 6.98(s,1H) ppm.

$^{13}$C NMR (75.4 MHz, CDCl$_3$): δ=24.55, 25.06, 28.12, 31.53, 39.32, 49.88, 56.85, 58.55, 65.70, 89.94, 71.77, 80.09, 130.33, 153.44, 167.24 and 180.53 ppm.

Analysis %: Found: C,64.54; H,9.42; N,3.31. C$_{23}$H$_{41}$NO$_6$ C,64.61;H,9.66; N,3.28.

(E)-Benzyl cis-4-{1-[2-(tert-butoxycarbonyl)-3-(2-methoxyethoxy)prop-1-enyl]-1-cyclopentanecarboxamido}-1-cyclohexanecarboxylate To a solution of (E)-1-[2-(tert-butoxycarbonyl)-3-(2-methoxyethoxy)prop-1-enyl]-1-cyclopentanecarboxylic acid (1.0 g, 3.04 mmol) in ethyl acetate (10.6 mL) under a nitrogen atmosphere at room temperature was added dimethylformamide (1 drop), pyridine (0.49 mL, 6.08 mmol) and thionyl chloride (0.28 mL, 3.95 mmol) and the mixture stirred at room temperature for 40 minutes. Benzyl cis-4-amino-1-cyclohexanecarboxylate p-toluenesulphonate (1.29 g, 3.19 mmol) was added at room temperature followed by triethylamine (1.27 mL, 9.12 mmol) and the mixture stirred at room temperature for 3 hours. The reaction mixture was diluted with distilled water (50 mL) and ethyl acetate (50 mL) and the layers separated. The ethyl acetate layer was washed with distilled water (2×50 mL), 1.0M aqueous hydrochloric acid solution (50 mL), dried (MgSO$_4$), filtered and concentrated under reduced pressure to give a brown oil (1.552 g). The crude product was purified by chromatography on silica by elution with hexane/ethyl acetate (1:1) to give, after combination and evaporation of appropriate fractions, the title compound as an oil (1.07 g, 65%).

$^{13}$C NMR (75 Hz, CDCl$_3$): δ=24.84, 25.19, 27.97, 28.95, 38.95, 39.66, 46.71, 55.59, 58.73, 65.19, 66.01, 70.25, 71.55, 80.98, 127.89, 128.06, 128.46, 133.06, 148.91, 174.06, 174.63 ppm.

Analysis %: Found: C,68.18; H,8.23; N,2.57. C$_{13}$H$_{45}$NO$_7$ C,68.48; H,8.34; N,2.58.

(E)-Benzyl cis-4-{1-[2-carboxy-3-(2-methoxyethoxy)prop-1-enyl]-1-cyclopentanecarboxamido}-1-cyclohexanecarboxylate Trifluoroacetic acid (1.7 mL) was added dropwise to (E)-benzyl cis-4-{1-[2-tert-butoxycarbonyl)-3-(2-methoxyethoxy)prop-1-enyl]-1-cyclopentanecarboxamido}-1-cyclohexanecarboxylate (1.0 g, 1.83 mmol) at 0° C., and the resulting solution stirred at room temperature for 24 hours. The reaction mixture was concentrated under reduced pressure and the residue stripped with toluene (3×10 mL) to remove further trifluoroacetic acid. The residue was dissolved in t-butyl methyl ether (50 mL) and washed with distilled water (6×10ml).

The organic phase was dried (MgSO$_4$), filtered and concentrated under reduced pressure to give a brown oil (0.835 g). The crude product 1.5 was purified by chromatography on silica by eluting with ethyl acetate/hexane (2:1) +1% acetic acid to give, after combination and evaporation of appropriate fractions, the title compound as colourless crystals after trituration with ether (720 mg, 80%), m.pt.= 90°–91° C.

Analysis %: Found: C,66.37; H,7.48; N,2.85. C$_{27}$H$_{37}$NO$_7$ C,66.51; H,7.65; N,2.87.

I claim:
1. A method of preparing a compound of formula (I):

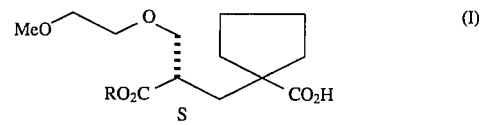

or an amine salt thereof wherein R is 5-indanyl or a carboxylic acid protecting group, which comprises hydrogenating an (E)-allylic ether of formula (II):

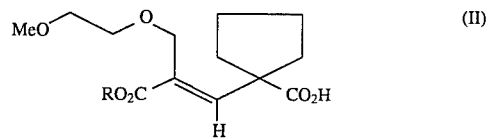

or an amine salt thereof where R is as defined for formula (I), in the presence of a stereoselective chiral rhodium or ruthenium biphosphine catalyst capable of catalysing said hydrogenation and a protic solvent.

2. A method according to claim 1, in which R is a C$_1$–C$_4$ alkyl group.

3. A method according to claim 2, in which R is t-butyl.

4. A method according to claim 1 in which said catalyst is a rhodium catalyst and an amine salt of the compound of formula (II) is hydrogenated.

5. A method according to claim 4, in which said amine salt is a cyclohexylamine or (1S,2S)-(+)-pseudoephedrine salt.

6. A method according to claim 4, in which the catalyst comprises the biphosphine ligand [(S)-(–)-2,2'bis(diphenylphosphino)-1,1'-binaphthyl](S)-(–)-2,2'-bis(diphenylphosphino)-1,1"-binaphthyl or (2S, 4S)-tert-butyl-4-(diphenylphosphine)-2-(diphenylphosphino)-2-diphenylphosphinomethyl-1-pyrrolidinecarboxylate.

7. A method according to claim 1 in which said catalyst is a ruthenium catalyst and the compound hydrogenated is an acid of formula (I) or a cyclohexylamine or (1S, 2S)-(+)-pseudoephedrine salt thereof.

8. A method of preparing a compound of formula (Ia):

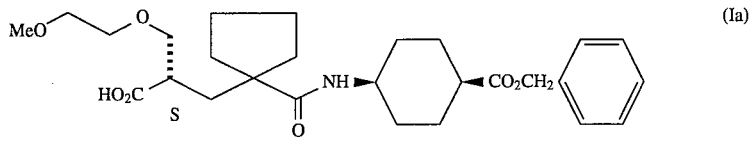

(Ia)

which comprises hydrogenating a compound of formula (IIa):

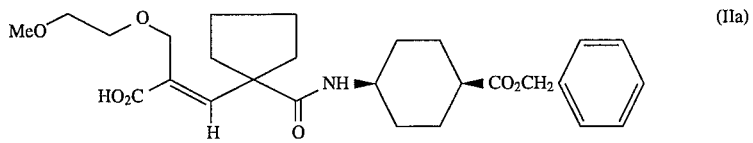

(IIa)

in the presence of a stereoselective chiral rhodium or ruthenium biphosphine catalyst capable of catalysing said hydrogenation, and a protic solvent.

9. A method according to claim 8, in which the catalyst comprises a ruthenium catalyst containing the biphosphine ligand R-(+)-2,2'-bis(diphenylphosphino)-1,1'-binaphthyl.

10. A method according to claim 8, in which the protic solvent is methanol or aqueous methanol.

11. A method according to claim 1 in which the protic solvent is methanol or aqueous methanol.

12. A method according to claim 2 in which said catalyst is a rhodium catalyst and an amine salt of the compound of formula (II) is hydrogenated.

13. A method according to claim 12, in which the catalyst comprises the biphosphine ligand [(S)-(–)-2,2'bis(diphenylphosphino)-1,1'-binaphthyl](S)-(–)-2,2'-bis(diphenylphosphino)-1,1"-binaphthyl or (2S, 4S)-tert-butyl-4-(diphenylphosphine)-2-(diphenylphosphino)-2-diphenylphosphinomethyl-1-pyrrolidinecarboxylate.

14. A method according to claim 12, in which said amine salt is a cyclohexylamine or (1S, 2S)-(+)-pseudoephedrine salt.

15. A method according to claim 14, in which the catalyst comprises the biphosphine ligand [(S)-(–)-2,2'bis(diphenylphosphino)-1,1'-binaphthyl](S)-(–)-2,2'-bis(diphenylphosphino)-1,1"-binaphthyl or (2S, 4S)-tert-butyl-4-(diphenylphosphine)-2-(diphenylphosphino)-2-diphenylphosphinomethyl-1-pyrrolidinecarboxylate.

16. A method according to claim 3, in which the catalyst comprises the biphosphine ligand [(S)-(–)-2,2'bis(diphenylphosphino)-1,1'-binaphthyl](S)-(–)-2,2'-bis(diphenylphosphino)-1,1"-binaphthyl or (2S, 4S)-tert-butyl-4-(diphenylphosphine)-2-(diphenylphosphino)-2-diphenylphosphinomethyl-1-pyrrolidinecarboxylate.

17. A method according to claim 16, in which the catalyst comprises the biphosphine ligand [(S)-(–)-2,2'bis(diphenylphosphino)-1,1'-binaphthyl](S)-(–)-2,2'-bis(diphenylphosphino)-1,1"-binaphthyl or (2S, 4S)-tert-butyl-4-(diphenylphosphine)-2-(diphenylphosphino)-2-diphenylphosphinomethyl-1-pyrrolidinecarboxylate.

18. A method according to claim 16 in which said amine salt is a cyclohexylamine or (1S, 2S)-(+)-pseudoephedrine salt.

19. A method according to claim 18, in which the catalyst comprises the biphosphine ligand [(S)-(–)-2,2'bis(diphenylphosphino)-1,1'-binaphthyl](S)-(–)-2,2'bis(diphenylphosphino)-1,1"-binaphthyl or (2S, 4S)-tert-butyl-4-(diphenylphosphine)-2-(diphenylphosphino)-2-diphenylphosphinomethyl-1-pyrrolidinecarboxylate.

20. A method according to claim 2 in which said catalyst is a ruthenium catalyst and the compound hydrogenated is an acid of formula (I) or a cyclohexylamine or (1S, 2S)-(+)-pseudoephedrine salt thereof.

21. A method according to claim 20, in which the protic solvent is methanol or aqueous methanol.

22. A method according to claim 3, in which the protic solvent is methanol or aqueous methanol.

\* \* \* \* \*